United States Patent [19]

Kravath

[11] 4,422,458

[45] Dec. 27, 1983

[54] METHOD AND APPARATUS FOR DETECTING RESPIRATORY DISTRESS

[75] Inventor: Richard E. Kravath, Dobbs Ferry, N.Y.

[73] Assignee: Montefiore Hospital and Medical Center, Inc., Bronx, N.Y.

[21] Appl. No.: 326,176

[22] Filed: Dec. 1, 1981

Related U.S. Application Data

[63] Continuation-in-part of Ser. No. 144,272, Apr. 28, 1980, abandoned.

[51] Int. Cl.³ .......................... A61B 5/04; A61B 5/05; A61B 5/08
[52] U.S. Cl. .................................... 128/671; 128/696; 128/723
[58] Field of Search ............... 128/671, 723, 670, 696, 128/709, 721, 716

[56] References Cited

U.S. PATENT DOCUMENTS

| | | | |
|---|---|---|---|
| 3,212,496 | 10/1965 | Preston | 128/671 |
| 3,572,317 | 3/1971 | Wade | 128/671 |
| 3,587,562 | 6/1971 | Williams | 128/671 X |
| 3,976,052 | 8/1976 | Junginger et al. | 128/671 |
| 4,031,884 | 6/1977 | Henzel | 128/671 X |
| 4,305,400 | 12/1981 | Logan | 128/670 |

Primary Examiner—Kyle L. Howell
Assistant Examiner—John C. Hanley
Attorney, Agent, or Firm—Hedman, Casella, Gibson, Costigan & Hoare

[57] ABSTRACT

A method and apparatus for detecting respiratory distress is disclosed wherein the increasing force of contraction of the heart, which occurs during a respiratory distress condition is detected and utilized to signal the condition. More particularly, the increasing force of contraction of a patient's heart, which affects the electrical signal generated by an impedance pneumograph may be detected by utilizing the heart beat of the patient to generate a trigger pulse. The trigger pulse is used as a timing means to enable the effects of the heart as registered on the impedance pneumograph, to be detected and compared, with an increase in amplitude of the contractions of the heart indicating a respiratory failure.

14 Claims, 2 Drawing Figures

METHOD AND APPARATUS FOR DETECTING RESPIRATORY DISTRESS

This is a continuation-in-part of application Ser. No. 144,272, filed Apr. 28, 1980 now abandoned.

BACKGROUND OF THE INVENTION

This invention relates to a method and apparatus for detecting respiratory distress conditions. More specifically, the subject invention provides a means for monitoring the output of a respiratory detector and differentiating between actual breaths and readings generated by the contractions of the patient's heart during respiratory arrest and using these readings to signal an alarm.

A variety of respiration monitors have been developed in the prior art for detecting the cessation of respiratory activity or apnea. One of the more common respiration monitors, an impedance pneumograph, measures the variations of the impedance in the thorax region of the body caused by movements of the chest during breathing. More specifically, as the patient breathes, and his chest alternately expands and contracts, the impedance of the thoracic cavity varies, and can be readily measured by existing electrical equipment. In a relatively simple embodiment of a prior art impedance pneumograph monitor, an alarm is connected to the device which is actuated when the variations of the output of the monitor cease, indicating respiratory arrest. In a typical intensive care situation, the sounding of the alarm alerts medical support personnel so that proper resuscitative procedures can be initiated.

The latter prior art respiration monitor, however, frequently fails to detect the onset of an apneic episode. More specifically, it has been found that the contractions of the patient's heart during respiratory arrest, often produces sufficient movement in the thoracic cavity to generate a varying output in the impedance pneumograph thereby preventing the associated alarm from being actuated. In order to obviate this shortcoming, various devices have been developed which utilize information from a cardiac monitor to increase the reliability of the device. For example, in U.S. Pat. No. 3,572,317 to Wade, an apnea monitor is disclosed which makes use of the clinical fact that during some apneic episodes, the heart rate tends to slow. The circuitry in Wade is designed to minitor both the heart and respiratory functions and to detect the situation where the heart rate is slowing. This information is correlated with output of the impedance pneumograph. More specifically, the circuitry in the Wade device is designed to detect the situation where both the contractions of the heart and the output of the impedance pneumograph are slowing at identical rates. When this situation exits it is likely that the output of the impedance pneumograph is merely a result of chest movements caused by the contractions of the heart rather than by actual breathing, and therefore an alarm will be sounded to indicate the apnea. One problem associated with the device disclosed in Wade is that a respiratory failure is not always immediately accompanied by a slowing of the heart rate. Thus, if a slowing of the heart rate does not occur relatively soon after a respiratory failure, the lack of oxygen in the body could result in damage prior to sounding of the alarm.

Another example of a prior art respiration monitor can be found in U.S. Pat. No. 3,976,052 to Juninger et al. The device disclosed in Junginger, similar to the Wade device, is concerned with the false breath-like output of the impedance pneumograph that is generated by the contractions of the patient's heart, and which would prevent the detection of an apneic episode. More specifically, the Junginger device utilizes that fact that during an apneic episode, the output of both the pneumograph and cardiograph, in terms of rate, will be substantially equal since the output of the former has been generated merely by the contractions of the heart. The circuitry in the Junginger device, therefore, compares the output received from the pneumograph and the cardiograph to determine if the heart rate and the apparent breathing rate are equal, and if such a situation exists, an alarm is sounded alerting the medical personnel. However, as can be appreciated, if the patient's breathing happens to coincide with his heart rate, the Junginger device might nevertheless indicate a stoppage of breathing, thereby disrupting both the patient and the medical staff. Thus, it would be desirable to provide an apnea monitor which is not solely dependent upon comparing the output of both a pneumograph and a cardiograph to determine if the frequencies of those outputs are equivalent. Further, it would be desirable to provide an apnea monitor which does not depend upon the slowing of the heart rate to signal the onset of respiratory failure.

As discussed more fully hereinbelow, the respiratory monitor of the subject invention satisfies these objects by combining the output produced by both an impedance pneumograph and an electrocardiograph in a novel manner. In contrast to the above described devices, the apparatus of the subject invention utilizes the clinical fact that during an apneic episode, the levels of oxygen in the body drop, while the levels of carbon dioxide rise. In response to this potentionally harmful situation, the forcefulness of the contractions of the patient's heart tends to increase in an attempt to increase blood circulation throughout the body to prevent the death of the cells due to lack of oxygen and excess carbon dioxide. The forcefulness of the contractions will continue to increase or will remain at a constant forceful level until the patient begins to breathe again or dies.

Accordingly, it is an object of the subject invention to provide a new and improved apparatus and method for detecting respiratory distress which utilizes the fact that the force of contractions of the heart tends to increase during an apneic episode and which combines the information generated by an impedance pneumograph and an electrocardiograph in a novel manner, in order to signal the onset of respiratory distress.

It is a further object of the subject invention to provide an apnea monitor which may be used alone or in conjunction with other apnea devices to increase the effectiveness of the latter.

It is another object of the subject invention to provide an apnea monitor which is not dependent upon the slowing of the heart rate of the patient to produce a warning signal.

It is still a further object of the subject invention to provide an apnea monitor that detects the increasing amplitude of the output of an impedance pneumograph which is a result of the increasing force of contraction of the heart.

It is still another object of the subject invention to provide an apnea monitor which utilizes the electrical currents generated by the heart as a trigger for determining the amplitude of the analog wave form of the impedance pneumograph such that the forceful contractions of the heart which correspond to a respiratory distress condition are detected.

SUMMARY OF THE INVENTION

In accordance with these and many other objects, applicant's invention provides for an apparatus which utilizes the output generated by an impedance pneumograph and electrocardiograph in a novel manner for detecting a respiratory distress condition. More particularly, the subject invention includes a means, such as an impedance pneumograph, which is connectable to the patient and provides an analog electrical signal corresponding to respiratory activity. A second generating means, such as an electrocardiograph, is provided for generating an electrical signal corresponding to the contractions of the heart. The subject invention further includes a digitizing means for determining the magnitude of the analog electrical signal generated by the impedance pneumograph. More particularly, the electrocardiograph signal is gated to the digitizing means so that the electrical currents generated by the heart of the patient just prior to the heart contractions generate a trigger pulse that activates the digitizing means. The digitizing means in turn, computes the amplitude of the output of the pneumograph at the instant it receives the trigger pulse. A comparator circuit is provided which stores the output of the digitizing means and compares the most recent amplitude computed by the digitizing means to previous amplitude, as described in detail below, to determine if the amplitudes of the output of the pneumograph steadily increase or remain constant over time. Subsequent paragraphs herein also describe how the comparator can screen out minor anomalies in an otherwise constant or steadily increasing pattern. If a constant or increasing pattern is detected, a signal is generated by the comparator means which may be used to actuate an alarm, signalling the onset of an apneic episode.

More specifically, and as noted above, during an apneic episode there is no breathing, and thus the contractions of the heart produce the only movements in the patient's thoracic region which are detected by the pneumograph. These forceful contractions of the heart during an apneic episode produce a pneumograph output with each successive amplitude equal to or greater than its predecessor. In order to accurately calculate the amplitude of the analog waves of the pneumograph output which are a result of cardiac activity, the electrical activity of the heart, as registered on the cardiograph, is used as a timing means to trigger the digitizing means. By this arrangement, the forceful contractions of the heart manifested in the output of the pneumograph are detected and the steady or increasing pattern is recognized. As a result, the onset of a respiratory distress condition is signaled.

The subject invention also may be used as an indicator in other situations where the force of a contraction of the heart increases. For example, in stressful circumstances or when a patient experiences a large blood loss, the force of contraction of the heart tends to increase and this occurrence also can be detected by the monitor of the subject invention.

Furhter objects and advantages of the subject invention will become apparent from the following detailed description when taken in conjunction with the accompanying drawings in which.

DESCRIPTION OF THE PREFERRED EMBODIMENT

Figure 1:
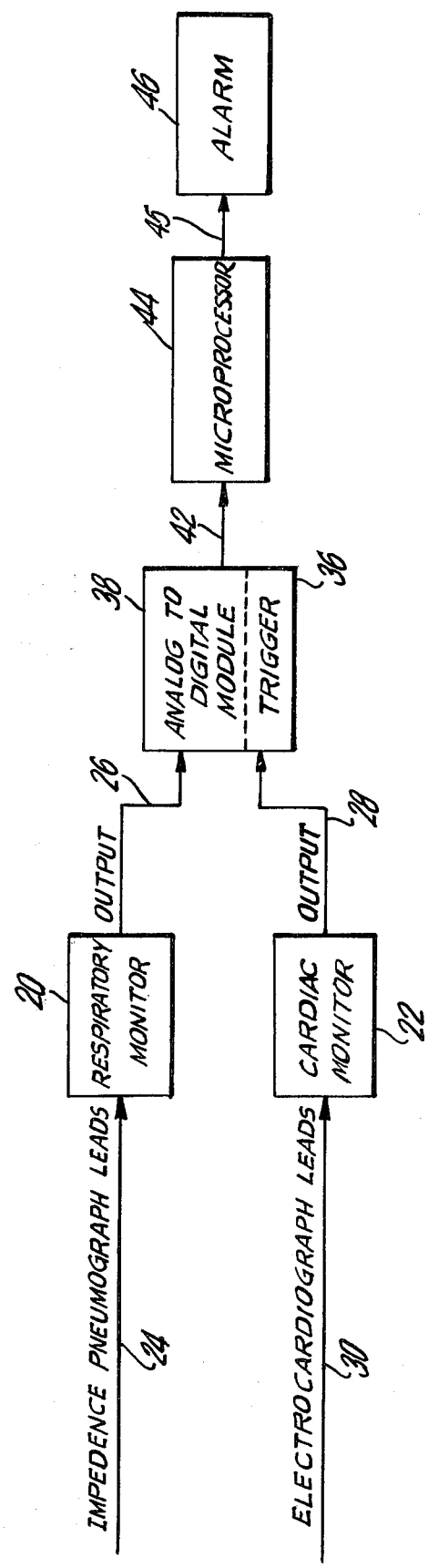
FIG. 1 is a schematic block diagram of the apnea detecting apparatus of the subject invention.

As illustrated in the schematic diagram of FIG. 1, the subject invention includes a pair of monitors connectable to a patient, and more specifically, a respiratory monitor 20 and a cardiac monitor 22. The respiratory monitor 20 may be of any known type which generates an electrical signal corresponding to the movements of the thoracic cavity. Preferably, an impedance pneumograph is utilized wherein leads 24 are placed on a patient's chest and the impedance therebetween is measured. As the patient breathes, the impedance of the thoracic cavity varies generating an electrical signal 26 as illustrated in FIG. 2.

A second monitor 22 is provided for generating an electrical signal 28 corresponding to the contractions of the heart of the patient. Preferably, the cardiac monitor is an electrocardiograph with leads 30 being connectable to a patient and fed into monitor 22. The electrocardiograph measures the electrical activity generated by the heart of the patient. The patient's heart contracts in response to these currents, such that the electrical signal generated by the cardiograph essentially corresponds to the contractions of a healthy heart. Both the impedance pneumograph and the electrocardiograph operate continuously and their output is graphicasly represented by tracings 26, 28 as is illustrated in FIG. 2. The central line 32 of FIG. 2 is a time line, with each interval A, between marks 34 corresponding to one half second time intervals.

Figure 2:
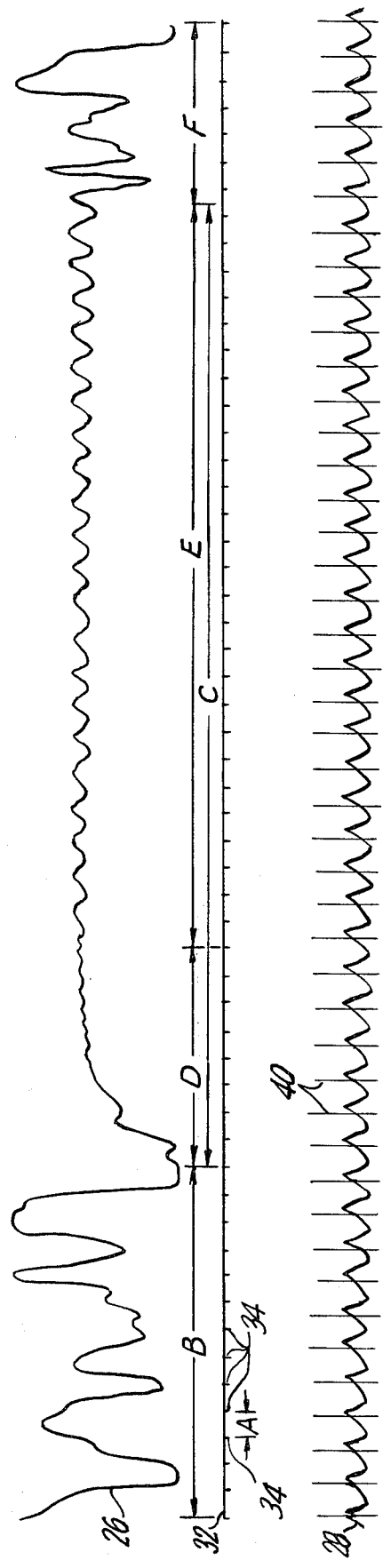
FIG. 2 is a graphical representation of the electrical outputs as a function of time, generated by an impedance pneumograph and an electrocardiograph, with the upper tracing corresponding to the former and the lower tracing corresponding to the latter.

The analog tracing 26 of FIG. 2 generated by the impedance pneumograph, illustrates a normal breathing pattern over the initial interval B, with the patient taking breaths every few seconds. The second interval C, extending for approximately 18 seconds, corresponds to an apneic episode wherein the patient has stopped breathing. The first portion of the apneic episode (interval D) illustrates little movement in the thoracic cavity of the patient. The latter portion of the apneic episode (interval E) illustrates an analog wave form in which each amplitude is either greater than or equal to its predecessor. This pattern, as shown by tracing 26 in interval E, is a result of thoracic movements generated by the contractions of the patient's heart. The increased force of contractions occurs because the heart is attempting to compensate for rapidly decreasing oxygen, and rising carbon dioxide levels in the body. The portion of tracing 26 to the far right of FIG. 2 (interval F) illustrates the restoration of normal breathing.

The electrocardiograph tracing 28 of FIG. 2, illustrates the typical cardiac wave form wherein the patient's heart is shown beating at a relatively constant rate of approximately 100 beats per minute.

The electrical tracings 26 and 28, which are obtainable from conventional medical monitors, are utilized in a novel manner in the subject invention to detect a respiratory distress condition. More specifically, and as illustrated in FIG. 1, at each instant 40, the electrical output 28 of cardiac monitor 22 generates a trigger pulse 36 for digitizing means 38. The digitizing means 38 determines the amplitude of the analog wave form of the pneumograph output 26 in response to the trigger pulse. By this arrangment, and as described more fully hereinbelow, the steady or increasing amplitude of the output 26 of the impedance pneumograph 20, which occurs during an apneic episode, can be monitored enabling the detection of the respiratory distress condition.

In operation, each electrical pulse 40 generated just prior to each contraction of the patient's heart actuates or triggers digitizing means 38 which determines the amplitude of the impedance pneumograph 26 at that particular instant. The digitized output 42 is then gated to a microprocessor 44 which determines if the amplitudes of the pneumograph output 26 reflect a steady increase or a constant pattern thereby indicating a respiratory distress condition. The microprocessor also is able to screen out minor anomalies during an apneic episode wherein one or two peaks on impedance pneumograph 26 may be less than their predecessor.

The microprocessor 44 is essentially a comparator means which is programmed to store the value of amplitudes and compare the amplitude of the most recently received digital electrical pulse 42 with the amplitude of a previously received pulse. For example, a simplified program to be utilized in conjunction with the microprocessor 44 so that the microprocessor 44 could detect a steadily increasing or constant trend, but also could screen out the minor anomalies referred to above, would include the following instructions:

1. Set pulse count equal to zero, where pulse count corresponds to the number of connective digital electrical pulses having an amplitude equal to or greater than the amplitude of the preceding digital electrical pulse;
2. Set AMP 2 equal to zero, where AMP 2 corresponds to the amplitude of the most recent received digital electrical pulse;
3. Set AMP 1 equal to zero, where AMP 1 corresponds to the amplitude of a previously received digital electrical pulse;
4. Set anomaly count equal to zero, where an anomaly refers to a digital electrical pulse occurring during an apneic episode wherein that pulse is less than its predecessor;
5. Set AMP 2 equal to the amplitude of the next pulse;
6. Add 1 to pulse count;
7. Does pulse count equal 1, if yes, go to step 8 otherwise go to step 9;
8. Set AMP 1 equal to AMP 2 and return to step 5;
9. Compare AMP 2 to AMP 1. If AMP 2 is equal to or greater than AMP 1, go to step 12, otherwise proceed to step 10.
10. Add 1 to anomaly count;
11. If anomaly count is greater than the accepted number of anomalies, return to step 1, otherwise return to step 5;
12. If pulse count is greater than or equal to a value corresponding to a distress condition, proceed, otherwise return to step 8;
13. Sound alarm signaling respiratory distress condition.

In the above described simplified program, the pulse count corresponding to the onset of a respiratory distress conditon may be adjusted in accordance with various factors, such as the condition or age of the particular patient. In most applications, a pulse count of 10 would be sufficiently high to virtually preclude the possibility of a false alarm. However, in human patients, the pulse count of 10 would correspond to an elapsed time of approximately 5 seconds, which would give hospital personnel ample time to respond to the alarm and begin the appropriate resuscitative measures. In the typical operation when the pulse count coresponding to the respiratory distress condition is equaled or exceeded, the microprocessor will generate electrical signal 45 which can be utilized, for example, to sound an alarm 46 for alerting medical personnel to begin resuscitative measures. In the alternative, the signal 45 generated by the microprocessor 44 could be used to activate life support systems already connected to the patient.

The anomaly count referred to in the above program accounts for the clinical fact that during an apneic episode, there may be an occassional slightly less forceful heartbeat, which will cause a smaller amplitude to be registered on impedance pneumograph tracing 26. It would be desirable not to have the program return to the beginning upon the occurrence of an anomaly. Conversely, if the program accepts too may anomalies, it would be susceptible to false alarms. In most instances, the accepted number of anomalies referred to in Step 11 above, would be set equal to 1. Although not shown in the above program, the anomaly subprogram could be modified to determine the percent by which the anomaly amplitude is less than its predecessor. This additional step would account for the fact that an anomaly in a continuing apneic episode would be only slightly less than its predecessor. Thus, for example, Step 10a might provide: If AMP 2 is less than 90% of AMP 1 return to Step 1 otherwise proceed.

The operation of the subject invention can be more readily understood with reference to the graphical representation in FIG. 2, illustrating a typical apneic episode. In the region of the graph of FIG. 2, designated as interval B, the patient is breathing normally and exhibits a corresponding wave form. During interval B, digital module 38, in response to the contractions 40 of the heart, generates pulses 42 having random amplitudes or values. At interval D, the patient undergoes a respiratory arrest, wherein there is little change in the impedance of the thoracic cavity thereby initially producing a relatively flat pneumograph tracing. As the apneic episode continues, the force of contractions of the heart increase in an effort to restore normal oxygen and carbon dioxide values. This increase in the force of contractions, causes increased movement in the thoracic cavity which appears on the pneumograph tracing 26 throughout interval E. Thus, during interval E, the output 42 from the digitizing module 38, which is triggered by the heart's contractions, increases in amplitude. The pulses 42, of increasing amplitude, are gated to the microprocessor 44 such that a comparison is made in accordance with the above described program. When the increasing trend lasts for a period corresponding to a respiratory distress condition, typically ten pulses, the microprocessor 44 generates an electrical signal 45 indicating that a respiratory distress condition exists. Electrical signal 45 can be used to activate alarm 46 for alerting the medical staff to begin life saving maneuvers in an attempt to restore normal breathing as indicated at interval F, of FIG. 2.

The apnea monitor of the subject invention may be used alone or in conjunction with other apnea monitors to increase the reliability of the latter. Further, the subect invention, which relies on the clinical observation that the force of contraction of the heart increases when there is a drop in oxygen levels in the body, can be employed for other uses. For example, where the patient experiences a sudden blood loss, the heart will also tend to contract more forcefully, thereby signaling the medical staff to this condition.

In summary, the subject invention provides for an apparatus for detecting a respiratory distress condition in a patient which includes the combining of information generated by conventional cardiac and respiratory monitors in a novel way. More particularly, the heart beat, registered by the cardiac monitor is used as a triggering means signaling a digitizing module 38 to determine the amplitude of the analog output of the respiratory monitor. The amplitude of the analog wave forms of the respiratory monitor are then compared to determine if they are increasing. Since the digitizing module 38 is triggered by contractions of the heart, the increasing amplitude of the pneumograph output can be attributed to the increasing force of the contractions of the patient's heart, rather than breathing. Accordingly, if the comparator means (microprocessor 44) detects a pneumograph output wherein the amplitudes are steadily increasing or remain constant, an electrical signal will be generated which may be used to actuate an alarm to alert support personnel of the condition.

Although the subject invention has been described by reference to a preferred embodiment, it is apparent that other modifications could be devised by those skilled in the art that would fall within the scope and spirit of the present invention as defined by the appended claims.

What is claimed is:

1. An apparatus for detecting a respiratory distress condition in a patient comprising:
    first generating means connectable to a patient for providing a first electrical signal corresponding to thoracic cavity activity;
    second generating means connectable to a patient for providing a second electrical signal corresponding to heart beat activity;
    trigger means coupled to said second generating means for providing an electrical trigger pulse corresponding to each heart beat;
    digitizing means coupled to said first generating means and said trigger means, said digitizing means being operative to produce a digital electrical pulse in response to each trigger pulse received from said trigger means, said digital electrical pulse corresponding to the amplitude of said first electrical signal of said first generating means; and
    comparator means coupled to said digitizing means for comparing the amplitude of the most recent digital electrical pulse generated by said digitizing means to the amplitude of the previous digital electrical pulse, and for counting the number of consecutive digital electrical pulses having an amplitude equal to or greater than the amplitude of the preceding digital electrical pulse, said comparator means being operative to produce a third electrical signal when each of a selected number of consecutive digital electrical pulses has an amplitude greater than or equal to the digital electrical pulse immediately preceeding it, the selected number of digital electrical pulses defining the desired sensitivity of said apparatus and being at least ten pulses, said third electrical signal corresponding to a respiratory distress condition.

2. An apparatus for detecting a respiratory distress condition as recited in claim 1 wherein said comparator means is operative so as to screen out up to two anomalous digital electrical pulses each of which has an amplitude less than the pulse immediately preceeding it, whereby anomalies in an otherwise constant or increasing pattern are disregarded by said comparator means.

3. An apparatus for detecting a respiratory distress condition as recited in claim 1 wherein said comparator means is operative to screen out one anomalous digital electrical pulse having an amplitude less than the pulse immediately preceeding it, whereby an anomaly in an otherwise constant or increasing pattern is disregarded by said comparator means.

4. An apparatus for detecting a respiratory distress condition as recited in claim 3 wherein said first generating means is an impedance pneumograph.

5. An apparatus for detecting a respiratory distress condition as recited in claim 4 wherein said second generating means is an electrocardiograph.

6. An apparatus for detecting a respiratory distress condition as recited in claim 1 further including an indicator means coupled to said comparator means, said indicator means for signaling a respiratory distress condition in response to the generation of said third electrical signal by said comparator means.

7. An apparatus for detecting a respiratory distress condition as recited in claim 6 wherein said indicator means is an alarm.

8. A method for detecting a respiratory distress condition in a patient comprising the steps of:
    generating a first analog electrical signal corresponding to the thoracic cavity activity of a patient;
    generating a second electrical signal corresponding to the heartbeat activity of the patient;
    generating a trigger pulse corresponding to each heartbeat indicated by said second electrical signal;
    converting said first analog electrical signal into digital electrical pulses, each said converting step occurring in response to each said trigger pulse, said digital electrical pulses corresponding to the amplitude of said first electrical signal;
    comparing the most recent digital electrical pulse with the previous digital electrical pulse;
    counting the number of consecutive digital electrical pulses having an amplitude equal to or greater than the preceding digital electrical pulse; and
    generating a third electrical signal when each of a selected number of consecutive digital electrical pulses has an amplitude equal to or greater than the digital electrical pulse immediately preceding it, the selected number of digital electrical pulses defining the desired sensitivity of said method and being at least ten pulses, said third electrical signal corresponding to a respiratory distress condition.

9. A method for detecting a respiratory distress condition as recited in claim 8 further comprising the step of screening out up to two anomalous digital electrical pulses each of which has an amplitude less than the pulse immediately preceding it, whereby anomalies in an otherwise constant or increasing pattern are disregarded.

10. A method for detecting a respiratory distress condition as recited in claim 8 further comprising the step of screening out one anomalous digital electrical pulse having an amplitude less than the pulse immediately preceding it, whereby an anomaly in an otherwise constant or increasing pattern is disregarded.

11. A method for detecting a respiratory distress condition as recited in claim 10 wherein said analog electrical signal corresponding to respiratory activity of a patent is generated by an impedance pneumograph.

12. A method of detecting a respiratory distress condition as recited in claim 11 wherein said second electrical signal corresponding to heart beat activity is generated by an electrocardiograph.

13. A method for detecting a respiratory distress condition as recited in claim 12 further including the step of producing an indication in response to the generation of said third electrical signal to thereby warn of the respiratory distress condition.

14. A method for detecting a respiratory distress condition as recited in claim 13 wherein said indication is an alarm.

* * * * *